(12) United States Patent
Abdou

(10) Patent No.: US 8,388,660 B1
(45) Date of Patent: Mar. 5, 2013

(54) DEVICES AND METHODS FOR SUPERIOR FIXATION OF ORTHOPEDIC DEVICES ONTO THE VERTEBRAL COLUMN

(76) Inventor: Samy Abdou, San Diego, CA (US)

( * ) Notice: Subject to any disclaimer, the term of this patent is extended or adjusted under 35 U.S.C. 154(b) by 475 days.

(21) Appl. No.: 11/888,754

(22) Filed: Aug. 1, 2007

Related U.S. Application Data

(60) Provisional application No. 60/834,644, filed on Aug. 1, 2006.

(51) Int. Cl.
A61B 17/70 (2006.01)

(52) U.S. Cl. ........................ 606/267; 606/313

(58) Field of Classification Search .................. 606/246, 606/264–279, 300–319; 411/29, 54.1, 57.1, 411/60.1, 71; 433/174
See application file for complete search history.

(56) References Cited

U.S. PATENT DOCUMENTS

| | | | |
|---|---|---|---|
| 3,708,883 A * | 1/1973 | Flander | 433/174 |
| 4,611,581 A * | 9/1986 | Steffee | 606/313 |
| 5,092,893 A | 3/1992 | Smith | |
| 5,098,435 A | 3/1992 | Stednitz et al. | |
| 5,122,131 A | 6/1992 | Tsou | |
| 5,129,899 A | 7/1992 | Small et al. | |
| 5,176,680 A | 1/1993 | Vignaud et al. | |
| 5,222,954 A | 6/1993 | Baker et al. | |
| 5,242,445 A | 9/1993 | Ashman | |
| 5,246,442 A | 9/1993 | Ashman et al. | |
| 5,261,909 A | 11/1993 | Sutterlin et al. | |
| 5,281,222 A | 1/1994 | Allard et al. | |
| 5,282,801 A | 2/1994 | Sherman | |
| 5,282,862 A | 2/1994 | Baker et al. | |
| 5,344,422 A | 9/1994 | Frigg | |
| 5,350,380 A | 9/1994 | Goble et al. | |
| 5,352,226 A | 10/1994 | Lin | |
| 5,360,431 A | 11/1994 | Puno et al. | |
| 5,403,316 A | 4/1995 | Ashman | |
| 5,423,818 A | 6/1995 | Van Hoeck et al. | |
| 5,423,819 A | 6/1995 | Small et al. | |
| 5,437,669 A | 8/1995 | Yuan et al. | |
| 5,437,670 A | 8/1995 | Sherman et al. | |
| 5,449,257 A | 9/1995 | Giannuzzi | |
| 5,466,237 A | 11/1995 | Byrd, III et al. | |
| 5,474,551 A | 12/1995 | Finn et al. | |
| 5,474,555 A | 12/1995 | Puno et al. | |
| 5,496,321 A | 3/1996 | Puno et al. | |
| 5,520,690 A | 5/1996 | Errico et al. | |
| 5,527,314 A | 6/1996 | Brumfield et al. | |
| 5,534,002 A | 7/1996 | Brumfield et al. | |
| 5,545,163 A | 8/1996 | Miller | |
| 5,562,661 A | 10/1996 | Yoshimi et al. | |
| 5,562,662 A | 10/1996 | Brumfield et al. | |
| 5,569,252 A | 10/1996 | Justin et al. | |
| 5,575,792 A | 11/1996 | Errico et al. | |
| 5,578,033 A | 11/1996 | Errico et al. | |
| 5,582,612 A | 12/1996 | Lin | |
| 5,584,833 A | 12/1996 | Fournet-Fayard et al. | |
| 5,584,834 A | 12/1996 | Errico et al. | |
| 5,609,593 A | 3/1997 | Errico et al. | |
| 5,609,594 A | 3/1997 | Errico et al. | |
| 5,611,800 A | 3/1997 | Davis et al. | |

(Continued)

Primary Examiner — Eduardo C Robert
Assistant Examiner — Steven Cotroneo
(74) Attorney, Agent, or Firm — Gazdzinski & Associates, PC

(57) ABSTRACT

A bone anchor is driven into the pedicle portion of the vertebral body until a shoulder protrusion within the proximal aspect of the anchor abuts the bone surface and prevents further anchor travel into the bone. A feature within the distal aspect of the anchor is actuated producing the emergence of a distal shoulder protrusion. The latter directly abuts the distal aspect of the pedicle at the pedicle/vertebral body interface. Using this method, the anchor captures the pedicle portion of bone and contains it between the proximal and distal shoulder abutments.

53 Claims, 9 Drawing Sheets

U.S. PATENT DOCUMENTS

| | | | |
|---|---|---|---|
| 5,616,142 A | 4/1997 | Yuan et al. | |
| 5,643,262 A | 7/1997 | Metz-Stavenhagen et al. | |
| 5,643,321 A * | 7/1997 | McDevitt | 606/232 |
| 5,647,873 A | 7/1997 | Errico et al. | |
| 5,649,931 A | 7/1997 | Bryant et al. | |
| 5,667,513 A | 9/1997 | Torrie et al. | |
| 5,669,911 A | 9/1997 | Errico et al. | |
| 5,672,176 A | 9/1997 | Biedermann et al. | |
| 5,688,275 A | 11/1997 | Koros et al. | |
| 5,690,630 A | 11/1997 | Errico et al. | |
| 5,713,904 A | 2/1998 | Errico et al. | |
| 5,733,285 A | 3/1998 | Errico et al. | |
| 5,752,957 A | 5/1998 | Ralph et al. | |
| 5,776,135 A | 7/1998 | Errico et al. | |
| 5,782,833 A | 7/1998 | Haider | |
| 5,810,818 A | 9/1998 | Errico et al. | |
| 5,810,819 A | 9/1998 | Errico et al. | |
| 5,817,094 A | 10/1998 | Errico et al. | |
| 5,873,878 A | 2/1999 | Harms et al. | |
| 5,884,702 A | 3/1999 | Yokley et al. | |
| 5,899,904 A | 5/1999 | Errico et al. | |
| 5,899,905 A | 5/1999 | Errico et al. | |
| 5,938,663 A | 8/1999 | Petreto | |
| 5,941,885 A | 8/1999 | Jackson | |
| 5,947,967 A | 9/1999 | Barker | |
| 5,951,558 A | 9/1999 | Fiz | |
| 5,961,518 A | 10/1999 | Errico et al. | |
| 5,976,135 A | 11/1999 | Sherman et al. | |
| 5,997,539 A | 12/1999 | Errico et al. | |
| 6,001,098 A | 12/1999 | Metz-Stavenhagen et al. | |
| 6,016,727 A | 1/2000 | Morgan | |
| 6,017,344 A | 1/2000 | Errico et al. | |
| 6,030,388 A | 2/2000 | Yoshimi et al. | |
| 6,033,406 A | 3/2000 | Mathews | |
| 6,045,555 A | 4/2000 | Smith et al. | |
| 6,048,343 A | 4/2000 | Mathis et al. | |
| 6,059,785 A | 5/2000 | Schavan et al. | |
| 6,063,089 A | 5/2000 | Errico et al. | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,096,060 A | 8/2000 | Fitts et al. | |
| 6,111,164 A | 8/2000 | Rainey et al. | |
| 6,123,706 A | 9/2000 | Lange | |
| 6,132,430 A | 10/2000 | Wagner | |
| 6,139,549 A | 10/2000 | Keller | |
| 6,159,210 A | 12/2000 | Voor | |
| 6,179,838 B1 | 1/2001 | Fiz | |
| 6,183,473 B1 | 2/2001 | Ashman | |
| 6,193,721 B1 | 2/2001 | Michelson | |
| 6,210,376 B1 | 4/2001 | Grayson | |
| 6,210,413 B1 | 4/2001 | Justis et al. | |
| 6,214,012 B1 * | 4/2001 | Karpman et al. | 606/304 |
| 6,224,602 B1 | 5/2001 | Hayes | |
| 6,228,085 B1 | 5/2001 | Theken et al. | |
| 6,231,575 B1 | 5/2001 | Krag | |
| 6,234,705 B1 | 5/2001 | Troxell | |
| 6,248,104 B1 | 6/2001 | Chopin et al. | |
| 6,248,105 B1 | 6/2001 | Schlapfer et al. | |
| 6,248,107 B1 | 6/2001 | Foley et al. | |
| 6,254,602 B1 | 7/2001 | Justis | |
| 6,258,089 B1 | 7/2001 | Campbell et al. | |
| 6,261,287 B1 | 7/2001 | Metz-Satavenhagen | |
| 6,273,889 B1 | 8/2001 | Richelsoph | |
| 6,280,442 B1 | 8/2001 | Barker et al. | |
| 6,283,967 B1 | 9/2001 | Troxell et al. | |
| 6,302,888 B1 | 10/2001 | Mellinger et al. | |
| 6,306,136 B1 | 10/2001 | Baccelli | |
| 6,306,137 B2 | 10/2001 | Troxell | |
| 6,315,779 B1 | 11/2001 | Morrison et al. | |
| 6,317,957 B1 | 11/2001 | Gregor et al. | |
| 6,355,039 B1 | 3/2002 | Troussel et al. | |
| RE37,665 E | 4/2002 | Ralph et al. | |
| 6,364,881 B1 | 4/2002 | Apgar et al. | |
| 6,371,957 B1 | 4/2002 | Amrein et al. | |
| 6,379,357 B1 | 4/2002 | Bernstein et al. | |
| 6,398,783 B1 | 6/2002 | Michelson | |
| 6,402,749 B1 | 6/2002 | Ashman | |
| 6,402,756 B1 | 6/2002 | Ralph et al. | |
| 6,413,259 B1 | 7/2002 | Lyons et al. | |
| 6,416,515 B1 | 7/2002 | Wagner | |
| 6,428,542 B1 | 8/2002 | Michelson | |
| 6,454,769 B2 | 9/2002 | Wagner et al. | |
| 6,471,703 B1 | 10/2002 | Ashman | |
| 6,503,250 B2 | 1/2003 | Paul | |
| 6,533,786 B1 | 3/2003 | Needham et al. | |
| 6,537,276 B2 | 3/2003 | Metz-Stacenhagen | |
| 6,554,834 B1 | 4/2003 | Crozet et al. | |
| 6,562,040 B1 | 5/2003 | Wagner | |
| 6,565,565 B1 | 5/2003 | Yuan et al. | |
| 6,582,436 B2 | 6/2003 | Schlapfer et al. | |
| 6,599,290 B2 | 7/2003 | Bailey et al. | |
| 6,602,257 B1 | 8/2003 | Thramann | |
| 6,613,050 B1 | 9/2003 | Wagner et al. | |
| 6,616,665 B2 | 9/2003 | Grafton et al. | |
| 6,620,163 B1 | 9/2003 | Michelson | |
| 6,626,904 B1 | 9/2003 | Jammet et al. | |
| 6,626,906 B1 | 9/2003 | Young | |
| 6,626,908 B2 | 9/2003 | Cooper et al. | |
| 6,641,583 B2 | 11/2003 | Shluzas et al. | |
| 6,641,586 B2 | 11/2003 | Varieur | |
| 6,648,887 B2 | 11/2003 | Ashman | |
| 6,648,894 B2 | 11/2003 | Abdelgany et al. | |
| 6,660,004 B2 | 12/2003 | Barker et al. | |
| 6,663,642 B2 | 12/2003 | Beyer et al. | |
| 6,668,688 B2 * | 12/2003 | Zhao et al. | 606/313 |
| 6,669,700 B1 | 12/2003 | Farris et al. | |
| 6,673,073 B1 | 1/2004 | Schafer | |
| 6,676,661 B1 | 1/2004 | Martin Benlloch et al. | |
| 6,685,705 B1 | 2/2004 | Taylor | |
| 6,695,846 B2 | 2/2004 | Richelsoph et al. | |
| 6,706,045 B2 | 3/2004 | Lin et al. | |
| 6,716,214 B1 | 4/2004 | Jackson | |
| 6,723,100 B2 | 4/2004 | Biedermann et al. | |
| 6,733,502 B2 | 5/2004 | Altarac et al. | |
| 6,736,817 B2 | 5/2004 | Troxell et al. | |
| 6,755,830 B2 | 6/2004 | Minfelde et al. | |
| 6,755,835 B2 | 6/2004 | Schultheiss et al. | |
| 6,832,999 B2 | 12/2004 | Ueyama et al. | |
| 6,835,196 B2 | 12/2004 | Biedermann et al. | |
| 6,858,030 B2 | 2/2005 | Martin et al. | |
| 6,887,242 B2 | 5/2005 | Doubler et al. | |
| 6,893,444 B2 | 5/2005 | Orbay | |
| 6,899,714 B2 | 5/2005 | Vaughan | |
| 6,945,972 B2 | 9/2005 | Frigg et al. | |
| 6,947,967 B2 | 9/2005 | Ferris et al. | |
| 6,949,100 B1 | 9/2005 | Venturini | |
| 6,951,561 B2 | 10/2005 | Warren et al. | |
| 7,022,122 B2 | 4/2006 | Amrein et al. | |
| 7,166,107 B2 | 1/2007 | Anderson | |
| 7,575,587 B2 | 8/2009 | Rezach et al. | |
| 7,582,107 B2 | 9/2009 | Trail et al. | |
| 7,604,643 B2 | 10/2009 | Ciccone et al. | |
| 7,744,635 B2 | 6/2010 | Sweeney et al. | |
| 7,938,848 B2 | 5/2011 | Sweeney et al. | |
| 2002/0045899 A1 | 4/2002 | Errico et al. | |
| 2002/0055738 A1 * | 5/2002 | Lieberman | 606/61 |
| 2002/0143332 A1 | 10/2002 | Lin et al. | |
| 2002/0143341 A1 | 10/2002 | Biedermann et al. | |
| 2002/0169450 A1 | 11/2002 | Lange | |
| 2002/0183748 A1 | 12/2002 | Martin et al. | |
| 2003/0000350 A1 | 1/2003 | Zhao et al. | |
| 2003/0023240 A1 | 1/2003 | Amrein et al. | |
| 2003/0045878 A1 | 3/2003 | Petit et al. | |
| 2003/0073997 A1 | 4/2003 | Doubler et al. | |
| 2003/0105460 A1 | 6/2003 | Crandall et al. | |
| 2003/0149431 A1 | 8/2003 | Varieur | |
| 2003/0149432 A1 | 8/2003 | Frigg et al. | |
| 2003/0171751 A1 | 9/2003 | Ritland | |
| 2003/0176864 A1 | 9/2003 | Ueyama et al. | |
| 2003/0208202 A1 | 11/2003 | Falahee | |
| 2004/0010253 A1 | 1/2004 | Morrison | |
| 2004/0092930 A1 | 5/2004 | Petit et al. | |
| 2004/0102780 A1 | 5/2004 | West, Jr. | |
| 2004/0147928 A1 | 7/2004 | Landry et al. | |
| 2004/0147929 A1 * | 7/2004 | Biedermann et al. | 606/61 |
| 2004/0181226 A1 | 9/2004 | Michelson | |

| | | | | | | |
|---|---|---|---|---|---|---|
| 2004/0215190 A1 | 10/2004 | Nguyen et al. | | 2006/0079903 A1 | 4/2006 | Wong |
| 2004/0236330 A1 | 11/2004 | Purcell et al. | | 2006/0089647 A1 | 4/2006 | Culbert et al. |
| 2004/0254574 A1 | 12/2004 | Morrison et al. | | 2006/0149234 A1 | 7/2006 | De Coninck |
| 2005/0070901 A1 | 3/2005 | David | | 2006/0149245 A1 | 7/2006 | Sweeney |
| 2005/0075636 A1 * | 4/2005 | Gotzen .................... 606/72 | | 2006/0195096 A1 | 8/2006 | Lee et al. |
| 2005/0113830 A1 | 5/2005 | Rezach et al. | | 2006/0235391 A1 * | 10/2006 | Sutterlin .................... 606/61 |
| 2005/0113833 A1 | 5/2005 | Davison | | 2007/0118122 A1 | 5/2007 | Butler et al. |
| 2005/0119748 A1 | 6/2005 | Reiley et al. | | | | |
| 2005/0277923 A1 | 12/2005 | Sweeney | | * cited by examiner | | |

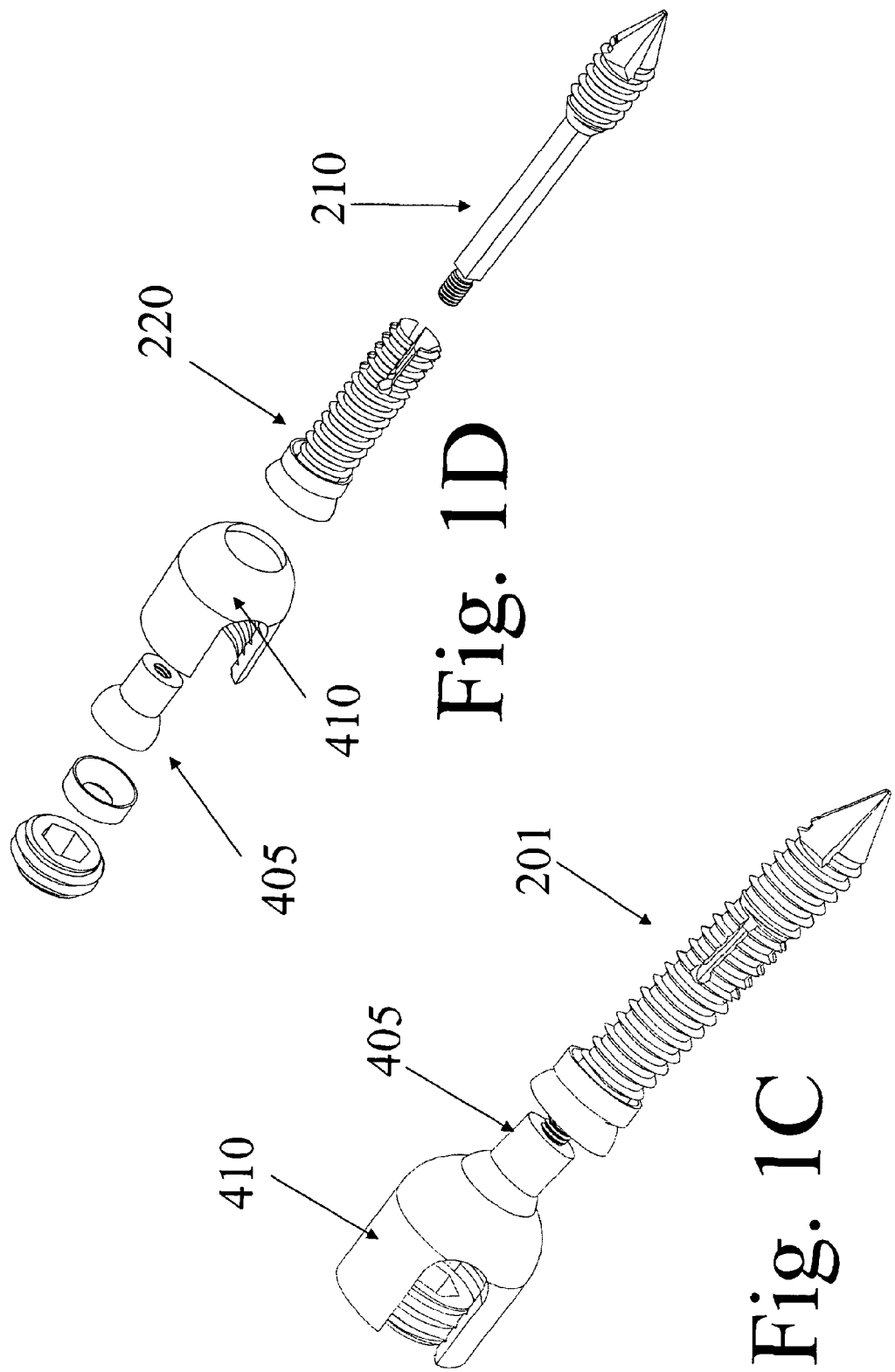

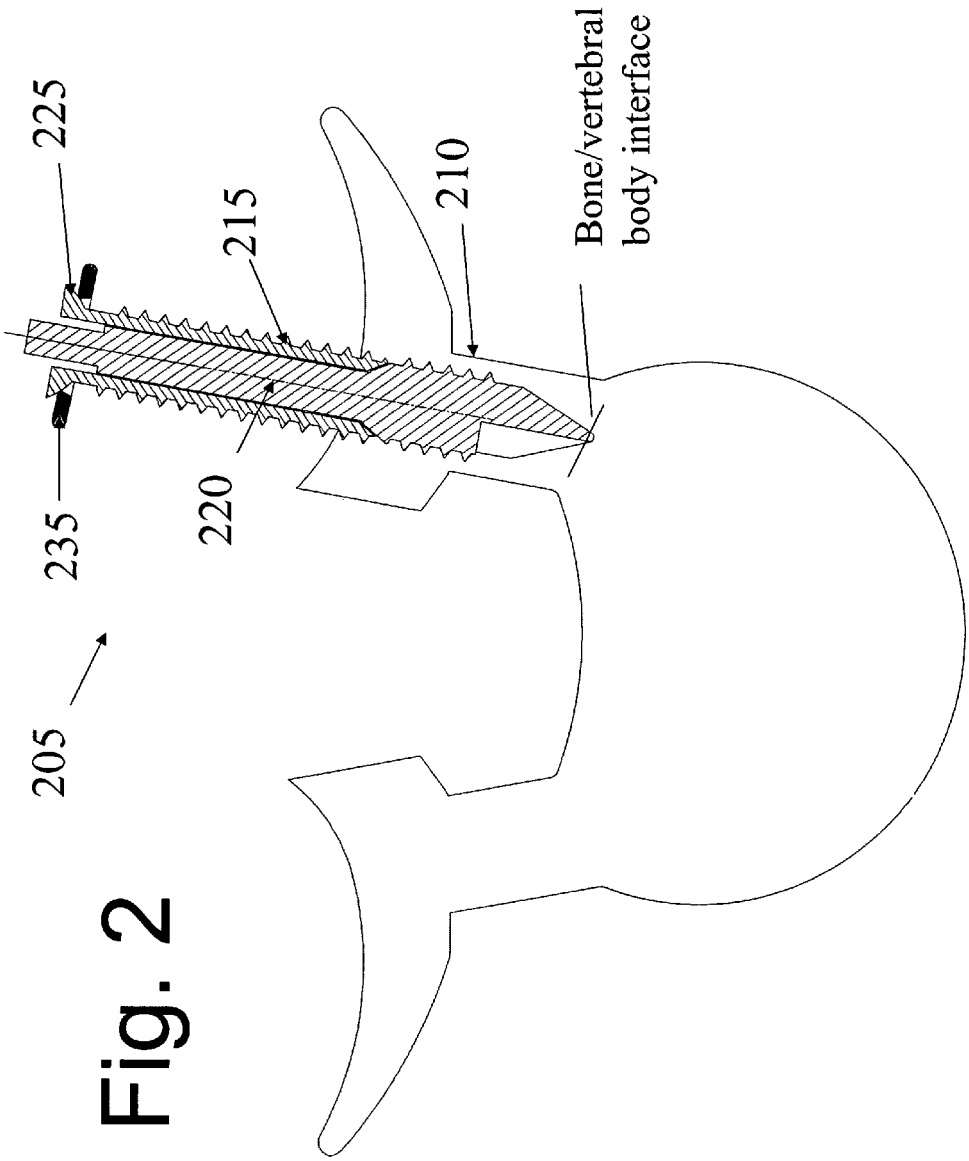

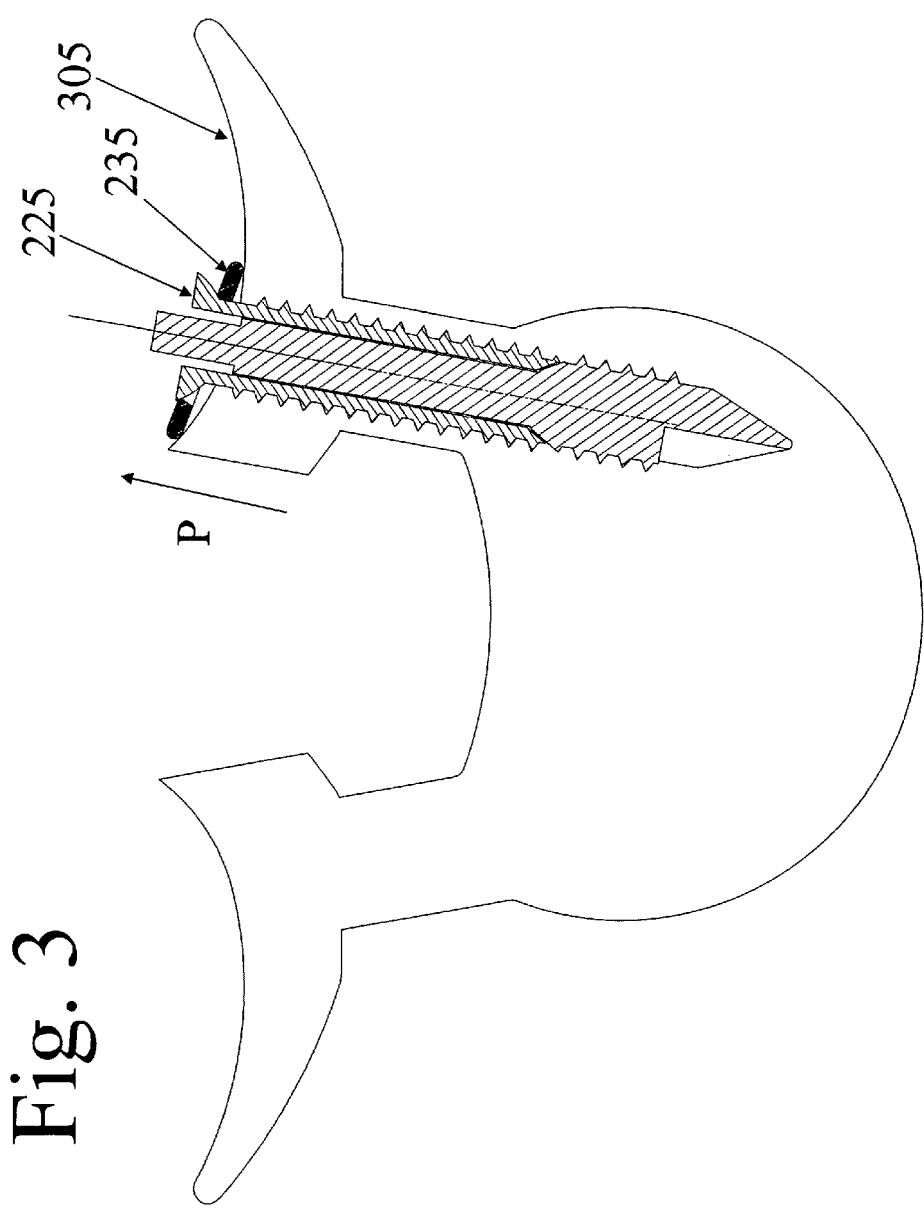

DEVICES AND METHODS FOR SUPERIOR FIXATION OF ORTHOPEDIC DEVICES ONTO THE VERTEBRAL COLUMN

REFERENCE TO PRIORITY DOCUMENT

This application claims priority of U.S. Provisional Patent Application Ser. No. 60/834,644, filed Aug. 1, 2006. Priority of the aforementioned filing date is hereby claimed and the disclosure of the Provisional Patent Applications is hereby incorporated by reference in its entirety.

BACKGROUND

The present disclosure is related to orthopedic devices implanted between skeletal segments. The implanted devices are used to adjust and maintain the spatial relationship(s) of adjacent bones. Depending on the implant design, the motion between the skeletal segments may be returned to normal, increased, modified, limited or completely immobilized.

Whether from degenerative disease, traumatic disruption, infection or neoplastic invasion, alterations in the anatomical relationships between the spinal vertebras can cause significant pain, deformity and disability. Spinal disease is a major health problem in the industrialized world and the surgical treatment of spinal pathology is an evolving discipline. The traditional surgical treatment of abnormal vertebral alignment and aberrant motion is the complete immobilization and bony fusion of the involved spinal segment. More recently, preservation of vertebral motion during the treatment of the spinal pathology has been the preferred strategy and many surgical techniques have been formulated to accomplish this treatment objective.

Regardless of whether the vertebral motion is abolished or preserved, many surgeons employ implantable orthopedic devices that adjust, align, support and/or maintain the spatial relationship(s) of the adjacent vertebral bones. The effectiveness of theses devices is vitally dependant on the adequacy of their fixation onto the underlying bone. Inadequate device fixation will effectively uncouple the device from the vertebral column and marginalize the beneficiary effects of the implant. Further, poorly anchored devices may damage the attached bone by fracturing and/or avulsing bone fragments at the attachment sites.

Screw fixation into the pedicle portion of the vertebral body has emerged as the most common method of device fixation onto the vertebral column. However, it is known that repeated loading and unloading of these screws will lead to screw loosening and eventual pull-out. Implantable devices that promote spinal fusion must bear load for the few months needed to produce bone graft maturation and solid vertebral fusion. In contrast, devices that preserve vertebral motion must bear the cyclical load of movement for the remainder of the patient's life. With the change in treatment strategy towards motion preservation, the integrity of the bone/device interface and the durability of the device fixation sites are emerging as major determinants of implant's functional life span.

SUMMARY

In attempt to improve screw fixation onto the vertebral bodies, a number of devices have been developed. Despite these improvements, there is still significant need for improved devices and methods for screw fixation onto the vertebral column. This need will increase further as surgeons widen the application of the motion preservation procedures.

This application discloses novel implant designs and methods of use. The illustrated embodiments provide superior anchor fixation onto the vertebral bones and significantly increase the resistance to anchor pull-out.

In an embodiment, a bone anchor is driven into the pedicle portion of the vertebral body until a shoulder protrusion within the proximal aspect of the anchor abuts the bone surface and prevents further anchor travel into the bone. A feature within the distal aspect of the anchor is actuated producing the emergence of a distal shoulder protrusion. The latter directly abuts the distal aspect of the pedicle at the pedicle/vertebral body interface. Using this method, the anchor captures the pedicle portion of bone and contains it between the proximal and distal shoulder abutments.

In another embodiment, the bone anchor is driven into the pedicle portion of the vertebral body and the distal aspect of the anchor is actuated producing the emergence of a distal shoulder protrusion. The anchor is gently backed-out of the vertebral bone until the distal shoulder protrusion is snugly lodged against the distal aspect of the pedicle at the pedicle/vertebral body interface. The anchor may be used to fixate orthopedic implants at this point. Alternatively, a proximal shoulder protrusion could be added and lodged against the bone surface at the anchor insertion site. This feature captures the pedicle portion of bone between two abutment surfaces and increase the anchor's fixation power and pull-out'resistance.

Other features and advantages will be apparent from the following description of various embodiments, which illustrate, by way of example, the principles of the disclosed devices and methods.

BRIEF DESCRIPTION OF THE DRAWINGS

FIG. 1C shows a perspective view of a pedicle screw system in an assembled state.

FIG. 1D shows a perspective view of the pedicle screw system in an exploded state.

FIG. 2 shows a shank system of a pedicle screw assembly partially inserted into a pedicle segment of a vertebral body.

FIG. 3 shows the shank system fully advanced into the bone such that a shoulder has moved toward the outer bone surface.

DETAILED DESCRIPTION

Figure 1B:
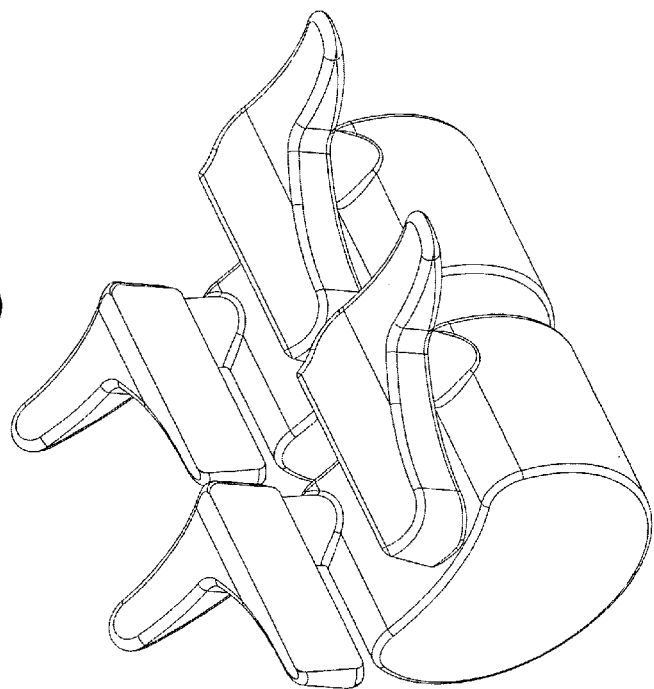
FIG. 1B shows the same vertebral bodies V1 and V2 after surgical resection of the lamina.
Figure 1A:
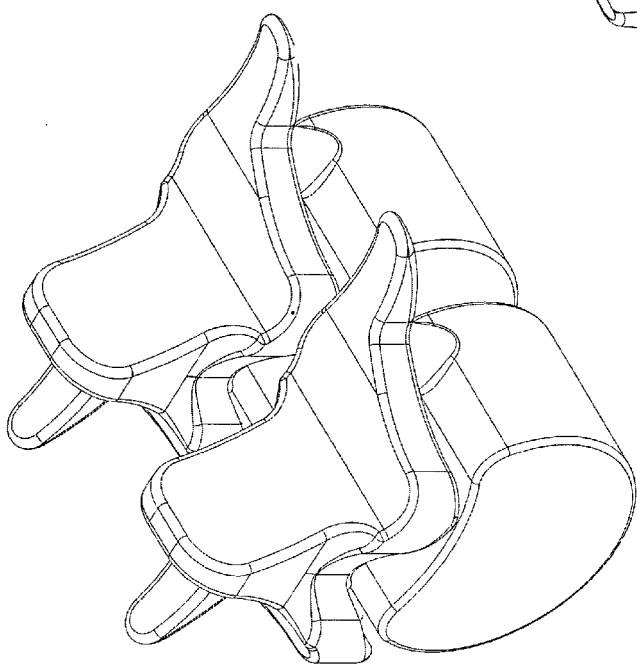
FIG. 1A shows two intact vertebral bodies V1 and V2.

FIG. 1A shows two intact vertebral bodies. For clarity of illustration, the vertebral bodies are represented schematically and those skilled in the art will appreciate that actual vertebral bodies include anatomical details not shown in FIG. 1A. For clarity of illustration, certain anatomical details, such as the patient's skin, are not shown in at least some of the figures. The vertebral arch is comprised of two pedicles, the short stout processes that extend from the sides of the vertebral body and two laminae, the broad flat plates that project from the pedicles and join in a triangle to form a hollow archway (the foramen). FIG. 1B illustrates the same vertebral bodies after surgical resection of the lamina. The negative effects of laminectomy can be countered by the reconstruction of the lamina.

FIG. 1C shows a perspective view of a pedicle screw assembly in an assembled state. FIG. 1D shows a perspective view of the pedicle screw assembly in an exploded state. The pedicle screw assembly employs a pedicle locking technique that provides powerful screw immobilization and reduces the possibility of loosening and movement with repeated loading. The pedicle screw assembly includes a includes a multi-piece shank system 201 comprising an inner shank member 210 that is slidably disposed within an outer shank member 215, as described in more detail below. The screw assembly 205 further includes a screw head member 405 and a receiver member 410 that collectively couple to the shank system, as described more fully below.

With reference to FIG. 2, the pedicle screw assembly 205 is partially inserted into a pedicle segment of the vertebral body. The pedicle screw assembly 205 employs a pedicle locking technique that provides powerful screw immobilization and reduces the possibility of loosening and movement with repeated loading. In this regard, after full insertion or deployment into the bone, the screw assembly 205 is configured to lock onto the outer and inner aspect of the pedicle so as to trap the pedicle, as described more fully below.

With reference to FIG. 2, the screw assembly 205 includes a multi-piece shank system comprising the inner shank member 210 that is slidably disposed within the outer shank member 215. The inner shank member 210 has a sharpened distal tip for penetrating the bone and also has a threaded outer surface along a distal region for screwing into bone. A proximal region 220 of the inner shank member 210 has a reduced radial size that slidably fits within the outer shank member 215.

The outer shank member 215 is slidably disposed over the proximal region 220 of the inner shank member 210. The outer shank member 215 is deformable and is configured to expand radially outward in response to advancement of the shank system into the bone, as described more fully below. A widened shoulder 225 is located at a proximal end of the outer shank member 215. The shoulder 225 has a convex outer surface that engages a locking member 235 that is washer-like. That is, the locking member 235 is ring-shaped and sized to fit around the shoulder 225 of the outer shank member 215. With advancement of the screw assembly 205 into the bone, the locking member 235 conforms to the outer surface of the bone as described in detail below. It should be appreciated that the outer surface of the shoulder 225 need not be convex, but can have other shapes that gradually widen moving away from the shank portion of the outer member 215.

The shank system can be rotated such that the threaded engagement between the threads and the bone causes the shank system to advance into the bone. FIG. 3 shows the shank system fully advanced into the bone such that the distal end of the inner shank member 210 has advanced deeper into the bone and the shoulder 225 has moved toward the outer bone surface 305. As the shoulder 225 moves toward the outer bone surface 305, the locking member 235 is urged in a proximal direction (as represented by arrow P in FIG. 3) relative to the convex surface of the shoulder 225. The gradually-widening configuration of the convex outer surface causes the locking member 235 to wedge between the shoulder 225 and the outer bone surface 305. The locking member 235 automatically adjusts its position to conform to the outer surface 305 of the bone as the shank system is advanced. This creates a locking engagement between the shank system (at the location of the shoulder 225 and locking member 235) and the outer surface 305 of the pedicle.

Figure 4:
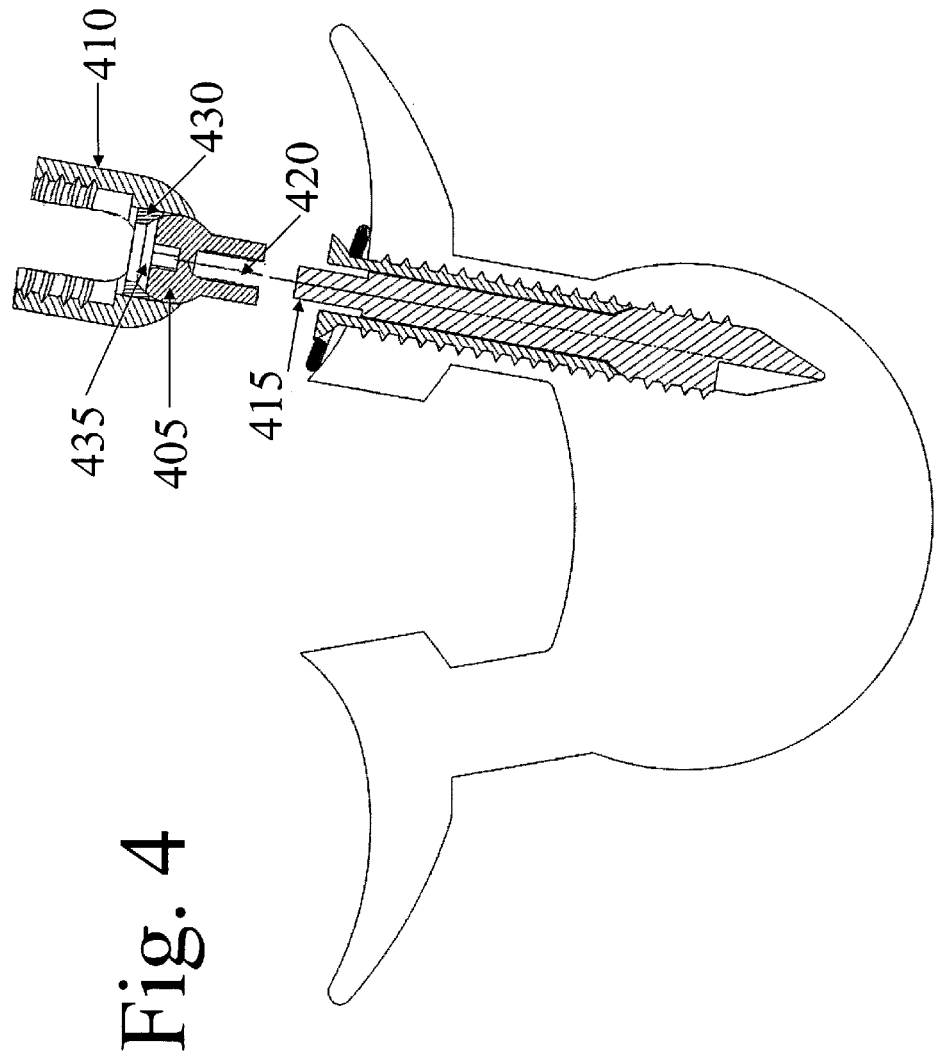
FIG. 4 shows a screw head and receiver being loaded onto the shank system.

As mentioned, the screw assembly 205 further includes a screw head member 405 and a receiver member 410 that collectively couple to the shank system. FIG. 4 shows the screw head member 405 and the receiver member 410 ready for coupling to the shank system. The head member 405 is adapted to removably couple to a protrusion 415 on the inner shank member 210. The protrusion 415 mates with a bore 420 in the head member 405, such as in a threaded male-female engagement or in any other mating engagement. The head member 405 is removably mounted in the receiver 410, as described below. The receiver 405 can include means, such as slots, adapted to receive an elongate stabilizer, or interconnecting member, such as a rod. It should be appreciated that the structure and type of engagement between the receiver 410 and the head member 405 can vary. For example, the engagement between the head member 405 and the receiver 410 can be a poly-axial or a mono-axial type engagement.

In an embodiment, there is a dynamic engagement between the head member 405 and the receiver member 410. In such an embodiment, the head member 405 is positioned within a multi-piece inner housing member 430 in which the head can rotate in a ball and socket manner. The inner housing member 430 can be immobilized relative to the receiver 410 to fixedly attach the head member 405 (and the attached shank system) to the housing. However, the head member 430 can rotate within the inner housing member 430 to permit some movement between the screw and the receiver 410. In addition, the head member 405 can be completely immobilized within the inner housing 430.

A space 435 is located within the inner housing member 430. The space 435 can contain a material or structure that resists movement of the head member 405 relative to the inner aspect of the inner housing members 430. The material or structure within the space 435 can be, for example, an elastic material(s), fluids, spring device(s), magnets or any other appropriate materials/devices that will resist movement of the head member 405 relative to the inner aspect of the inner housing members 430. When the screw head is moved out of a predetermined position in the inner housing members 430, the material/device within space 435 will apply a force to the head member 405 and resist any bone screw movement away from a neutral position. With movement, the assembly would return the screw and the attached bone to the neutral position once a deflecting force has dissipated. Further, before locking the assembly with a locking nut 610 (FIG. 6), the surgeon can freely adjust the orientation of the shank system relative to receiver 410 without influencing the assembly's neutral position or pre-loading the screw and bone construct.

Figure 5:
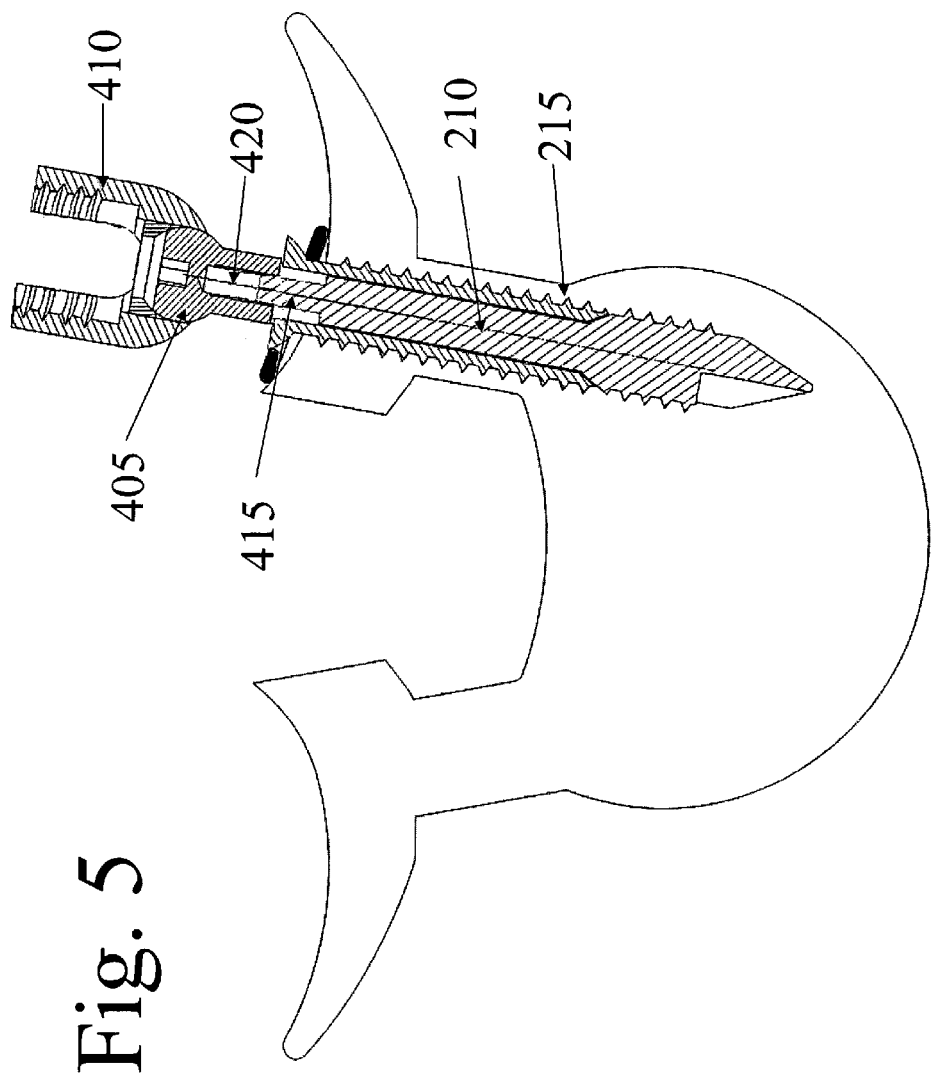
FIG. 5 shows the screw head and receiver being coupled onto the shank system.

FIG. 5 shows the head member 405 and the receiver 410 being coupled onto the shank system. As mentioned, the head member 405 can couple to the inner shank member 210 by threading the protrusion 415 into the bore 420 in the head member 405. The head member 405 is rotated about the protrusion 415 to cause the head member 405 (and attached receiver 410) to advance distally relative to the shank system. The distal advancement of the head member 405 over the protrusion 415 causes the outer shank member 215 to deform such that the outer shank member 215 expands radially outward.

Figure 6:
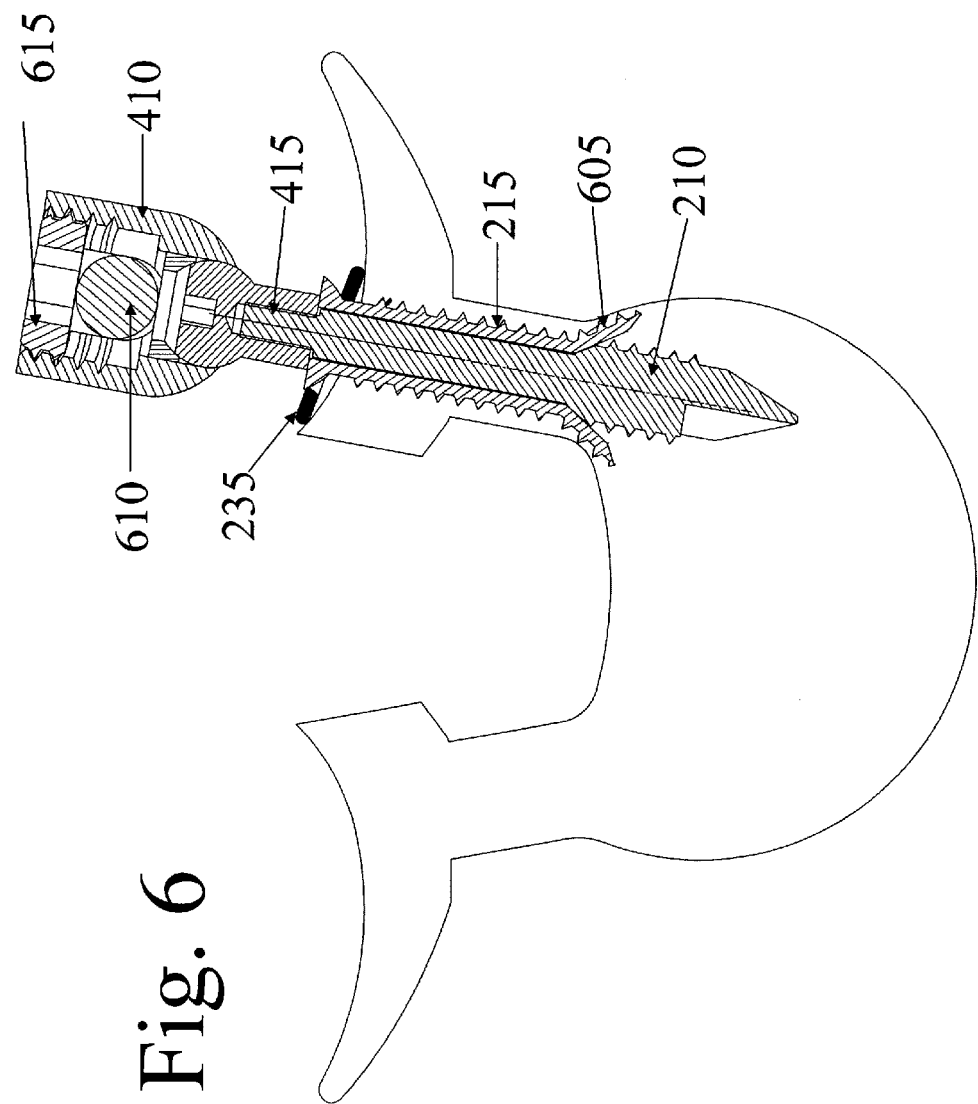
FIG. 6 shows the screw head and receiver fully coupled onto the shank system.

FIG. 6 shows the head member 405 and the receiver 410 fully coupled onto the shank system. The advancement of the head member 405 onto the protrusion 405 of the inner shank member 210 has caused a portion 605 of the outer shank member 215 to expand radially outward relative to the inner shank member 210. Thus, the portion 605 is forced against the inner aspect of the pedicle. In this way, the pedicle is captured and locked between the locking member 235 and the expanded portion 605 of the outer shank member 215. An interconnecting rod 610 can be coupled to the receiver 410 and secured thereto using a locking nut 615.

Figure 7:
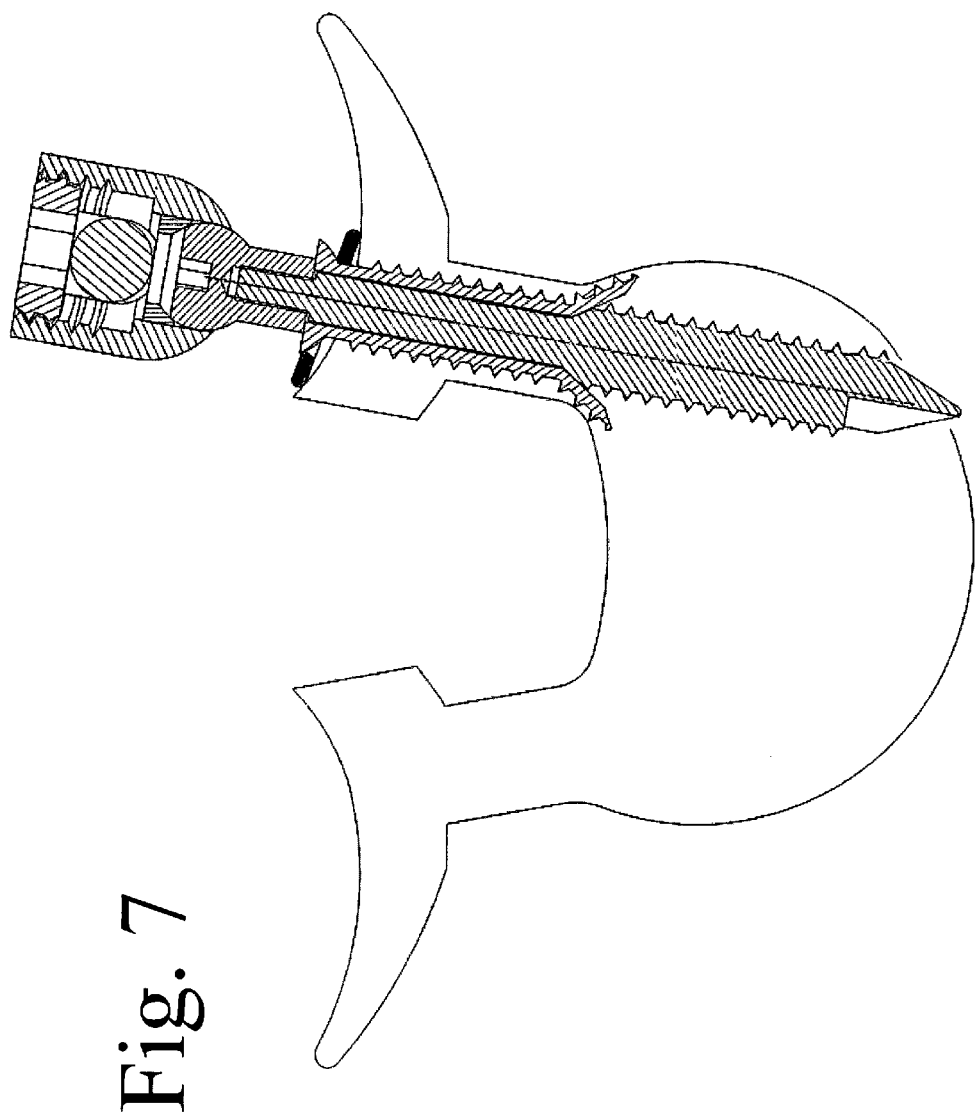
FIG. 7 shows a screw assembly that has a shank system of increased length.
Figure 8:
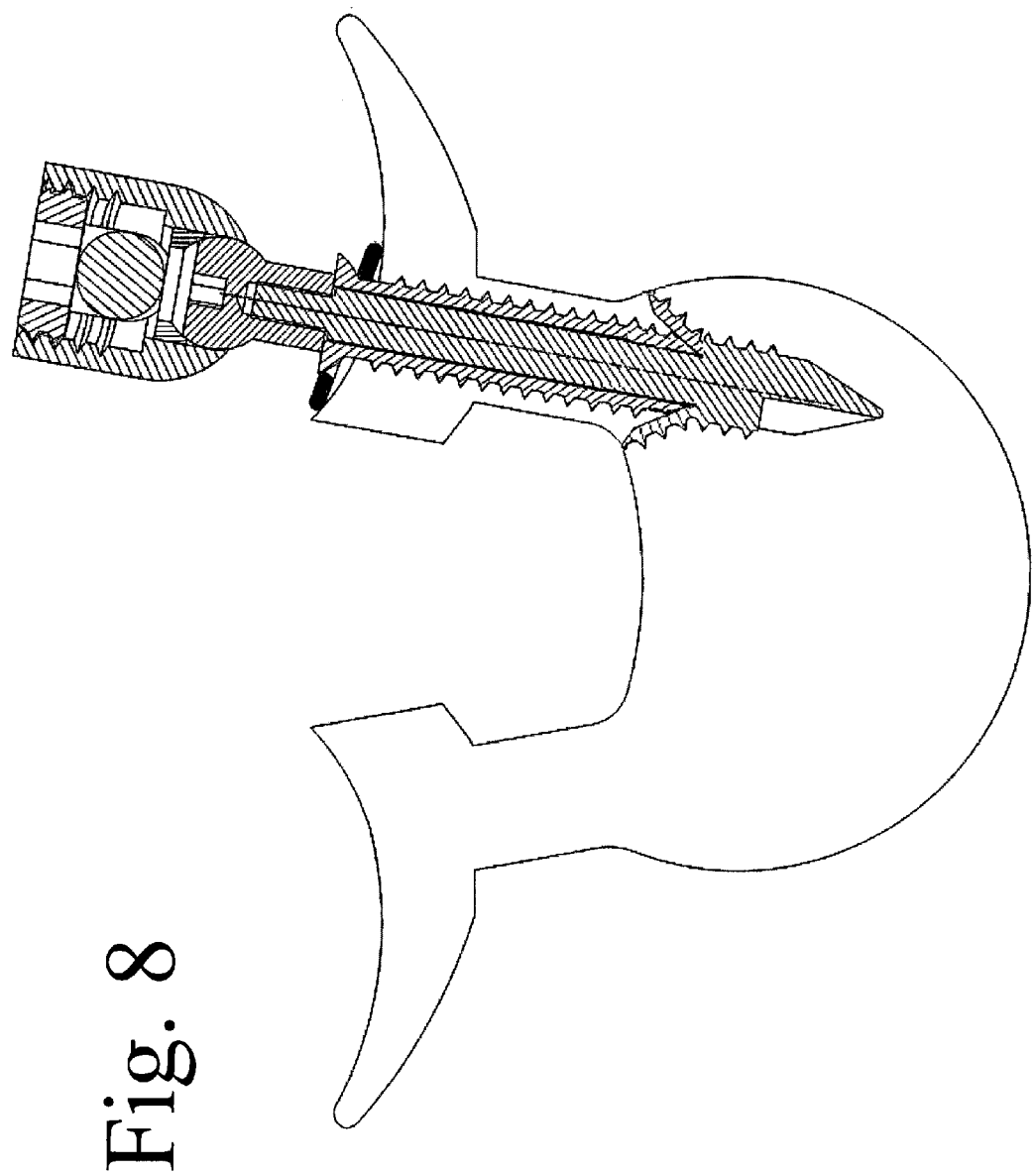
FIG. 8 shows another embodiment of the pedicle screw system.

It should be appreciated that the configuration of the screw assembly can be varied. In an embodiment, the shank system has an increased length that permits increased anchoring. FIG. 7 shows a similar screw assembly that has a shank system that is of greater length than the previously-described embodiment. The longer assembly permits anchor of the distal end of the shank into the anterior cortical surface of the vertebral body. Such an arrangement provides increased contact strength between screw and bone. Alternatively, the screw may be driven in a more superior trajectory so as to capture the superior cortical surface of the vertebral body. FIG. 8 shows another embodiment of the screw assembly. In this embodiment, the expanded portion expands outward in the opposite direction with respect to the previous embodiment.

The disclosed anchors may be at least partially made of bone or a bone graft substitutes. In addition, any device and any of its components can be made of any biologically adaptable or compatible materials. Materials considered acceptable for biological implantation are well known and include, but are not limited to, stainless steel, titanium, tantalum, combination metallic alloys, various plastics, resins, ceramics, biologically absorbable materials and the like. Any components may be also coated/made with osteo-conductive (such as deminerized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface may be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. In addition, the system or any of its components can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An orthopedic bone anchor assembly, comprising:
   an elongated outer shank member having external threads, an internal bore aligned along a long axis of the outer shank member, and at least one slot on a distal region of the outer shank member that permits radial expansion of the distal region of the outer shank member;
   an elongated inner shank member having a threaded distal segment and a proximal segment joined at an intersection, wherein the diameter of the distal segment is greater than the diameter of the proximal segment, and wherein, when the inner shank member is coupled to the outer shank member, at least a portion of the proximal segment is contained within the internal bore of the outer shank member, wherein at least a portion of the distal segment is threaded and positioned distally outside of the internal bore of the outer shank member; and
   a proximal head member having a threaded bore that engage a threaded proximal portion of the inner shank member, the head member further having a distal abutment surface that abuts a proximal portion of the outer shank member, wherein the head member is at least partially seated within a housing member, wherein the housing member is adapted to receive an interconnecting rod member, wherein the housing member is movable relative to the threaded shank member in at least one plane, and wherein the housing member contains a locking feature that is adapted to secure the interconnecting rod member to the housing member;
   wherein, a distance between the intersection and the distal abutment surface of the proximal head member varies with rotation of the proximal head member relative to the inner shank member; and
   wherein rotation of the proximal head member relative to the inner shank member produces (a) longitudinal movement of the inner shank member relative to the outer shank member, (b) advancement of the intersection against the distal region of the outer shank member, and (c) radial expansion of the distal region of the outer shank member.

2. An orthopedic bone anchor assembly, comprising:
   an elongated outer shank member having external threads, an internal bore aligned along a long axis of the outer shank member, and a distal region having a tapered tip;
   an elongated inner shank member having a threaded distal segment and a proximal segment joined at an intersection, and wherein the diameter of the threaded distal segment is greater than the diameter of the proximal segment, and wherein, when the inner shank member is coupled to the outer shank member, at least a portion of the proximal segment is contained within the internal bore of the outer shank member and wherein at least a portion of the distal segment includes expansion slots within an outer wall; and
   a proximal head member having a threaded bore that engages a thread proximal segment of the inner shank and a distal abutment surface that abuts a proximal region of the outer shank member, wherein the head member is at least partially seated within a housing member, wherein the housing member is adapted to receive an interconnecting rod member, wherein the housing member is movable relative to the threaded shank member in at least one plane, and wherein the housing member contains a locking feature that is adapted to secure the interconnecting rod member to the housing member;
   wherein rotation of the proximal head member relative to the inner shank member produces (a) longitudinal movement of the inner shank member relative to the outer shank member and radial expansion of the distal segment of the inner shank member; and
   wherein the inner and outer shank members remain attached together and collectively anchored to the bone after the bone anchor assembly is completely implanted in bone.

3. A method for the fixation of an orthopedic implant onto a vertebral bone, comprising:
   advancing a bone anchor member of a bone screw assembly through a bony surface of a first vertebral body and along a long axis of a pedicle portion of the vertebral bone, wherein the bone screw assembly comprises:

(a) an elongated bone anchor member having a shank portion of a first diameter that is adapted to penetrate and engage pedicle portion of the vertebral bone, wherein a threaded distal region of the elongated bone anchor member is adapted to expand within the vertebral bone after advancement of at least a portion of the shank portion distal to the pedicle portion of bone; and (b) an abutment member of a diameter greater than the first diameter of the shank portion, wherein the abutment member is adapted to abut the bony surface of the vertebral bone adjacent to a location where the elongated bone anchor member penetrates the bone;

driving the bone screw assembly into the vertebral bone until the abutment member abuts the bony surface of the vertebral bone adjacent to the location where the elongated bone anchor member penetrates the bone;

expanding the distal region of the elongated bone anchor member until a segment of the expanded distal region abuts a distal aspect of the pedicle portion of bone; and capturing the pedicle portion of bone between the expanded distal region of the elongated bone anchor member and the abutment member.

4. A bone fixation assembly, comprising:

a threaded shank member adapted to anchor onto bone and having an outer wall that is at least partially threaded, wherein the threaded shank member extends distally along a central axis from a proximal aspect, wherein the threaded shank member comprises at least a proximal threaded shank segment and a distal threaded shank segment, and wherein the proximal and distal threaded shank segments are axially aligned and movable relative to one another along the direction of the central axis;

a head segment that is connected to the proximal aspect of the proximal threaded shank segment, wherein the head segment is at least partially seated within a housing member, wherein the housing member is adapted to receive an interconnecting rod member, wherein the housing member is movable relative to the threaded shank member in at least one plane, and wherein the housing member contains a locking feature that is adapted to secure the interconnecting rod member to the housing member;

wherein the proximal threaded shank segment is divided into a proximal portion and a distal portion, wherein the distal portion of the proximal threaded shank segment abuts a proximal portion of the distal threaded shank segment, wherein the distal portion of the proximal threaded shank segment contains at least one expansion slot within a portion of the outer wall, wherein the expansion slot permit radial outward expansion of at least a portion of the outer wall of the distal portion of the proximal threaded shank segment.

5. A bone fixation assembly as in claim 4, wherein, when in the expanded state, the distal portion of the proximal threaded shank segment is of greater diameter than the proximal portion of the proximal threaded shank segment.

6. A bone fixation assembly as in claim 4, wherein, when in the expanded state, the distal portion of the proximal threaded shank segment is of greater diameter than at least a part of the distal threaded shank segment.

7. A bone fixation assembly as in claim 4, wherein a most distal aspect of the distal threaded shank segment is tapered in order to facilitate penetration of bone.

8. A bone fixation assembly as in claim 4, wherein the distal portion of the proximal threaded shank segment contains a plurality of expansion slots within a portion of the outer wall.

9. A bone fixation assembly as in claim 4, wherein axial movement of the distal threaded shank segment towards the proximal threaded shank segment along the central axis produces forcible expansion of the expansion slots of the distal portion of the proximal threaded shank segment.

10. A bone fixation assembly as in claim 4, wherein engagement of a threaded segment of a distal threaded shank segment provides a compressive force that drives the proximal and distal threaded shank segments towards one another and expands the expansion slots of the distal portion of the proximal threaded shank segment.

11. A bone fixation assembly as in claim 4, wherein a proximal abutment member is connected to the proximal aspect of the threaded shank member, wherein the abutment member is of greater diameter than the diameter of the threaded shank member, and wherein the abutment member is adapted to abut the bony surface of the vertebral bone adjacent to the location where the shank member anchors to the bone.

12. A bone fixation assembly as in claim 4, wherein the proximal abutment member articulates with the threaded shank member.

13. A bone fixation assembly as in claim 4, wherein the proximal abutment is movable relative to the threaded shank member in at least one plane.

14. A bone fixation assembly as in claim 4, wherein the head segment forms a ball and socket articulation with the inner seat of the housing member.

15. A bone fixation assembly as in claim 4, wherein the bone fixation assembly is at least partially manufactured from a Titanium alloy.

16. A bone fixation assembly as in claim 4, wherein the bone fixation assembly is at least partially manufactured from a memory shape alloy.

17. A bone fixation assembly as in claim 4, wherein the bone fixation assembly has at least one porous in-growth surface that is adapted to promote bone in-growth into the implant surface and establish a mineralized connection between the vertebral bone and the implant.

18. A bone fixation assembly as in claim 4, wherein the shank member of the bone anchor assembly has at least one porous in-growth surface that is adapted to promote bone in-growth into the implant surface and establish a mineralized connection between the vertebral bone and the implant.

19. A bone fixation assembly as in claim 4, wherein at least a portion of the bone anchor assembly is provided with a bioactive coating in order to promote a mineralized connection between the vertebral bone and the implant.

20. A method for the fixation of an orthopedic implant onto a vertebral bone, comprising:

advancing a bone anchor assembly through a bony surface of a first vertebral body and along a long axis of a pedicle portion of the vertebral bone, wherein the anchor assembly comprises:

a threaded shank member adapted to anchor onto bone and having an outer wall that is at least partially threaded, wherein the threaded shank member extends distally along a central axis from a proximal aspect, wherein the threaded shank member is comprised of at least a proximal threaded shank segment and a distal threaded shank segment, and wherein the proximal and distal threaded shank segments are axially aligned and movable relative to one another along the direction of the central axis; and a head segment that is connected to the proximal aspect of the proximal threaded shank segment, wherein the head segment is at least partially seated within a housing member, wherein the housing member is adapted to receive an interconnecting rod member, wherein the housing member is movable relative to the threaded shank member in at least one plane, and wherein the housing member contains a locking feature that is adapted to secure the interconnecting rod member to the housing member;

wherein the proximal threaded shank segment is divided into a proximal portion and a distal portion, wherein the distal portion of the proximal threaded shank segment abuts a proximal portion of the distal threaded shank segment, wherein the distal portion of the proximal threaded shank segment contains at least one expansion slot within a portion of the outer wall, wherein the expansion slot permit radial outward expansion of at least a portion of the outer wall of the distal portion of the proximal threaded shank segment, and wherein, when in the expanded state, the distal portion of the proximal threaded shank segment is of greater diameter than the proximal portion of the proximal threaded shank segment;

advancing the bone anchor assembly until the distal end of the distal threaded shank segment rests within the vertebral body;

moving the distal threaded shank segment along the central axis and towards the proximal threaded shank segment; and producing forcible expansion of the expansion slot of the proximal threaded shank segment, wherein, when in the expanded state, the expanded distal portion of the proximal threaded shank segment rests within the vertebral body.

21. A method for the fixation of an orthopedic implant onto a vertebral bone as in claim 20, wherein the expanded distal portion of the proximal threaded shank segment rests within the vertebral body but outside of the pedicle portion of bone.

22. A method for the fixation of an orthopedic implant onto a vertebral bone as in claim 20, wherein, after full implantation of the bone anchor assembly, the pedicle portion of the vertebral bone is positioned between the expanded distal portion of the proximal threaded shank segment and the housing member.

23. A bone fixation assembly, comprising:
a threaded shank member adapted to anchor onto bone and having an outer wall that is at least partially threaded, wherein the threaded shank member extends distally along a central axis from a proximal aspect, wherein the threaded shank member is comprised of at least a proximal threaded shank segment and a distal threaded shank segment, and wherein the proximal and distal threaded shank segments are axially aligned and movable relative to one another along the direction of the central axis; and
a head segment that is connected to the proximal aspect of the proximal threaded shank segment, wherein the head segment is at least partially seated within a housing member, wherein the housing member is adapted to receive an interconnecting rod member, wherein the housing member is movable relative to the threaded shank member in at least one plane, and wherein the housing member contains a locking feature that is adapted to secure the interconnecting rod member to the housing member;
wherein the distal threaded shank segment is divided into a proximal and a distal portion, wherein the proximal portion of the distal threaded shank segment abuts a distal portion of the proximal threaded shank segment, wherein the proximal portion of the distal threaded shank segment contains at least one expansion slot within a portion of the outer threaded wall, wherein the expansion slot permits radial outward expansion of at least a portion of the outer wall of the proximal portion of the distal threaded shank segment.

24. A bone fixation assembly as in claim 23, wherein, when in the expanded state, the proximal portion of the distal threaded shank segment is of greater diameter than the distal portion of the distal threaded shank segment.

25. A bone fixation assembly as in claim 23, wherein when in the expanded state, the proximal portion of the distal threaded shank segment is of greater radial size than at least a segment of the proximal threaded shank segment.

26. A bone fixation assembly as in claim 23, wherein a most distal aspect of the distal threaded shank segment is tapered in order to facilitate penetration of bone.

27. A bone fixation assembly as in claim 23, wherein the proximal portion of the distal threaded shank segment contains a plurality of expansion slots within a portion of the outer wall.

28. A bone fixation assembly as in claim 23, wherein axial movement of the distal threaded shank segment towards the proximal threaded shank segment along the central axis produces forcible expansion of the expansion slots of the proximal portion of the distal threaded shank segment.

29. A bone fixation assembly as in claim 23, wherein engagement of a threaded segment of the a distal threaded shank segment provides a compressive force that drives the proximal and distal threaded shank segments towards one another and expand the expansion slots of the proximal portion of the distal threaded shank segment.

30. A bone fixation assembly as in claim 23, wherein a proximal abutment member is connected to the proximal aspect of the threaded shank member, wherein the abutment member is of greater diameter than the diameter of the threaded shank member, and wherein the abutment member is adapted to abut the bony surface of the vertebral bone adjacent to the location where the shank member anchors to the bone.

31. A bone fixation assembly as in claim 23, wherein the proximal abutment member articulates with the threaded shank member.

32. A bone fixation assembly as in claim 23, wherein the proximal abutment is movable relative to the threaded shank member in at least one plane.

33. A bone fixation assembly as in claim 23, wherein the head member forms a ball and socket articulation with the inner seat of the housing member.

34. A bone fixation assembly as in claim 23, wherein the bone anchor assembly is at least partially manufactured from a Titanium alloy.

35. A bone fixation assembly as in claim 23, wherein the bone anchor assembly is at least partially manufactured from a memory shape alloy.

36. A bone fixation assembly as in claim 23, wherein the bone anchor assembly has at least one porous in-growth surface that is adapted to promote bone in-growth into the implant surface and establish a mineralized connection between the vertebral bone and the implant.

37. A bone fixation assembly as in claim 23, wherein the shank member of the bone anchor assembly has at least one porous in-growth surface that is adapted to promote bone in-growth into the implant surface and establish a mineralized connection between the vertebral bone and the implant.

38. A bone fixation assembly as in claim 23, wherein at least a segment of the bone anchor assembly is provided with a bioactive coating in order to promote a mineralized connection between the vertebral bone and the implant.

39. A method for the fixation of an orthopedic implant onto a vertebral bone, comprising:
advancing a bone anchor assembly through a bony surface of a first vertebral body and along a long axis of a pedicle portion of the vertebral bone, wherein the anchor assembly comprises:
a threaded shank member adapted to anchor onto bone and having an outer wall that is at least partially threaded, wherein the threaded shank member extends distally along a central axis from a proximal aspect, wherein the threaded shank member is comprised of at least a proximal threaded shank segment and a distal threaded shank segment, and wherein the proximal and distal threaded shank segments are axially aligned and movable relative to one another along the direction of the central axis; and
a head segment that is connected to the proximal aspect of the proximal threaded shank segment, wherein the head segment is at least partially seated within a housing member, wherein the housing member is adapted to receive an interconnecting rod member, wherein the housing member is movable relative to the threaded shank member in at least one plane, and wherein the housing member contains a locking feature that is adapted to secure the interconnecting rod member to the housing member;
wherein the distal threaded shank segment is divided into a proximal and a distal portion, wherein the proximal portion of the distal threaded shank segment abuts a distal portion of the proximal threaded shank segment, wherein the proximal portion of the distal threaded shank segment contains at least one expansion slot within a portion of the outer threaded wall, wherein the expansion slot permits radial outward expansion of at least a portion of the outer wall of the proximal portion of the distal threaded shank segment;
advancing the bone anchor assembly until the distal end of the distal threaded shank segment rests within the vertebral body;
moving the distal threaded shank segment along the central axis and towards the proximal threaded shank segment; and
producing forcible expansion of the expansion slot of the proximal threaded shank segment, wherein, when in the expanded state, the expanded distal portion of the proximal threaded shank segment rests within the vertebral body.

40. A method for the fixation of an orthopedic implant onto a vertebral bone as in claim 39, wherein the expanded proximal portion of the distal threaded shank segment rests within the vertebral body.

41. A method for the fixation of an orthopedic implant onto a vertebral bone as in claim 39, wherein, after full implantation of the bone anchor assembly, the pedicle portion of the vertebral bone is positioned between the expanded proximal portion of the distal threaded shank segment and the housing member.

42. A method for the fixation of an orthopedic implant onto a vertebral bone, comprising:
advancing a shank member of a bone anchor assembly through a bony surface of a first vertebral body and along a long axis of a pedicle portion of the vertebral bone, wherein the bone anchor assembly is comprised of at least a shank member of a first diameter that is adapted to the penetrate and engage a distal aspect of the pedicle portion of the vertebral bone, and wherein the shank member is adapted to expand within the vertebral bone;
expanding the shank member so as to form a first abutment surface and positioning the first abutment surface at the distal aspect of the pedicle portion of bone
positioning a second surface to abut the bony surface of the vertebral bone adjacent to the location where the shank member penetrates the vertebral bone, wherein the second abutment surface has diameter greater than the first diameter of the shank member and wherein the first and second abutment surfaces are collectively contained within the bone anchor assembly; and
capturing the pedicle portion of the vertebral bone between the first abutment surface formed by the expanded portion of the shank and the second abutment surface.

43. A method for the fixation of an orthopedic implant onto a vertebral bone as in claim 42, wherein the bone anchor assembly is at least partially manufactured from a Titanium alloy.

44. A method for the fixation of an orthopedic implant onto a vertebral bone as in claim 42, wherein the bone anchor assembly is at least partially manufactured from a memory shape alloy.

45. A method for the fixation of an orthopedic implant onto a vertebral bone as in claim 42, wherein the bone anchor assembly has at least one porous in-growth surface that is adapted to promote bone in-growth into the implant surface and establish a mineralized connection between the vertebral bone and the implant.

46. A method for the fixation of an orthopedic implant onto a vertebral bone as in claim 42, wherein the shank member of the bone anchor assembly has at least one porous in-growth surface that is adapted to promote bone in-growth into the implant surface and establish a mineralized connection between the vertebral bone and the implant.

47. A method for the fixation of an orthopedic implant onto a vertebral bone as in claim 42, wherein at least a segment of the bone anchor assembly is provided with a bioactive coating in order to promote a mineralized connection between the vertebral bone and the implant.

48. A method for the fixation of an orthopedic implant onto a vertebral bone, comprising:
advancing a shank member of a bone anchor assembly distally through a bony surface of a first vertebral body and along a long axis of a pedicle portion of the vertebral bone, wherein the bone anchor assembly is comprised of at least a shank member of a first diameter that is adapted to the penetrate and engage a distal aspect of the pedicle portion of the vertebral bone, and wherein the shank member is adapted to expand within the vertebral bone;
expanding the shank member so as to form a first abutment surface inside the vertebral bone;
moving the expanded first abutment surface proximally until the first abutment surface is lodged against the distal aspect of the pedicle at an interface between the pedicle and the vertebral body;
positioning a second surface to abut the bony surface of the vertebral bone adjacent to the location where the shank member penetrates the vertebral bone; wherein the first and second abutment surfaces are collectively contained within the bone anchor assembly; and
capturing the pedicle portion of the vertebral bone between the first abutment surface formed by the expanded portion of the shank and the second abutment surface.

49. A method for the fixation of an orthopedic implant onto a vertebral bone as in claim 48, wherein the bone anchor assembly is at least partially manufactured from a Titanium alloy.

50. A method for the fixation of an orthopedic implant onto a vertebral bone as in claim 48, wherein the bone anchor assembly is at least partially manufactured from a memory shape alloy.

51. A method for the fixation of an orthopedic implant onto a vertebral bone as in claim 48, wherein the bone anchor assembly has at least one porous in-growth surface that is adapted to promote bone in-growth into the implant surface and establish a mineralized connection between the vertebral bone and the implant.

52. A method for the fixation of an orthopedic implant onto a vertebral bone as in claim 48, wherein the shank member of the bone anchor assembly has at least one porous in-growth surface that is adapted to promote bone in-growth into the implant surface and establish a mineralized connection between the vertebral bone and the implant.

53. A method for the fixation of an orthopedic implant onto a vertebral bone as in claim 48, wherein at least a segment of the bone anchor assembly is provided with a bioactive coating in order to promote a mineralized connection between the vertebral bone and the implant.

* * * * *